(12) United States Patent
del Mar Serra et al.

(10) Patent No.: US 8,377,487 B2
(45) Date of Patent: Feb. 19, 2013

(54) MIXTURE OF CITRIC FLAVONOIDS TO IMPROVE RUMINAL FERMENTATION

(75) Inventors: Maria del Mar Serra, Barcelona (ES); Fernando Heredia, Barcelona (ES); Francisco Javier Crespo, Barcelona (ES); Joaquim Balcells, Barcelona (ES)

(73) Assignee: Exquim, S.A., Barcelona (ES)

( * ) Notice: Subject to any disclaimer, the term of this patent is extended or adjusted under 35 U.S.C. 154(b) by 261 days.

(21) Appl. No.: 12/812,208

(22) PCT Filed: Jan. 8, 2009

(86) PCT No.: PCT/EP2009/050175
§ 371 (c)(1),
(2), (4) Date: Jul. 8, 2010

(87) PCT Pub. No.: WO2009/087194
PCT Pub. Date: Jul. 16, 2009

(65) Prior Publication Data
US 2010/0291239 A1    Nov. 18, 2010

(30) Foreign Application Priority Data
Jan. 9, 2008  (EP) .................................... 08150133

(51) Int. Cl.
*A61K 31/35* (2006.01)
*A23K 1/16* (2006.01)
*A23K 1/18* (2006.01)

(52) U.S. Cl. .............................. 426/2; 424/442; 424/438
(58) Field of Classification Search ................... 424/442
See application file for complete search history.

(56) References Cited

U.S. PATENT DOCUMENTS
4,061,732 A * 12/1977 Muir et al. .................... 424/117

OTHER PUBLICATIONS

Han et al,"Studies on Antimicrobial Activities and Safety of Natural Naringin in Korea," Korean Journal of Mycology, Mar. 1988, abstract only.*
Haibo Hu et al; "Application of citrus pulp in animal production", Feed Industry; vol. 27, Issue 13; 2006.
Li Ping, Lu; "Minerals for animal feed", Information for Geological Technology in Jiangsu Province, Issue 3; 1993.
Taiwanese Examination Report issued on Oct. 24, 2012 in Taiwanese Patent Application No. 098100588 (English tranlsation attached).

* cited by examiner

*Primary Examiner* — Daniel Sullivan
*Assistant Examiner* — Rachael E Bredefeld
(74) *Attorney, Agent, or Firm* — Birch, Stewart, Kolasch & Birch, LLP

(57) ABSTRACT

The invention refers to the use of a mixture of naringin, bitter orange extract and sepiolite to improve ruminal fermentation in ruminants.

14 Claims, No Drawings

MIXTURE OF CITRIC FLAVONOIDS TO IMPROVE RUMINAL FERMENTATION

This invention refers to the use of a mixture of citric flavonoids to improve ruminal fermentation.

ABBREVIATIONS

VFA Volatile fatty acids
ΔCt Increase in amplification cycles.
ΔΔCt Increase in amplification cycles relative to the control samples in PCR
DGGE Denaturing gradient gel electrophoresis
*M. elsdenii Megasphaera elsdenii*
ns Not significant
PCR Polymerase chain reaction
*S. bovis Streptococcus bovis*

Mammals do not have appropriate digestive enzymes for the digestion of structural carbohydrates, i.e. cellulose. Therefore, and in order to access such an important source of nutrients, herbivores have developed fermentation compartments housing symbiotic flora which is capable of digesting or fermenting such nutrients. These compartments are located either prior to enzyme digestion in the host (ruminants) or subsequent to same (post-gastric fermenters, i.e. equids, rabbits). The rumen's microorganisms only partly use these carbohydrates and release volatile fatty acids (acetic, propionic and butyric acid), which are the most important source of energy for ruminants, as fermentation products. The microorganisms proliferating in the rumen are those which are capable of adapting to the compartment's conditions and using ingested food. The different food fractions, carbohydrates and proteins, are fermented and VFA production is supplemented by the surplus biomass generated in the rumen, which is, in turn, the main source of the protein finally absorbed in the duodenum.

Cellulose-fermenting bacteria (cellulolytic) grow optimally at a pH of 6.4-7 and produce more acetic acid than starch and sugar fermenting species (amylolytic). Their optimal pH is around 5.5 and when these levels decrease there is an increase in the relative production of lactic acid.

With the intensification of ruminant production systems, fodder-based feeding has been replaced by the administration of concentrated rations formulated with cereals which increase growth rates and reduce operating costs. Concentrated rations or the replacement of structural carbohydrates (cellulose) by rapidly fermenting soluble carbohydrates (starch), however, leads to the appearance of some digestive dysfunctions, such as acidosis and timpanism.

Ruminal acidosis can be defined as the digestive alteration produced by ingesting large quantities of food rich in fermentable carbohydrates and it is one of the most common dysfunctions in fattening calves. It can lead to death and starts by changing the bacterial population from gram negative to gram positive, favouring the development of species such as *S. bovis* or *Megasphaera elsdenii* and altering the proportion of VFAs. The proportion of acetic and propionic acid decreases, with an increase in butyric and lactic acid. The increase in lactic acid affects ruminal motility, producing meteorism due to the inability to eliminate the gas produced. Acute symptoms are anorexia, greenish-yellow aqueous faeces, ruminal atony, limping, abdominal retraction and dehydration. Subacute forms comprise frequent meteorism, abnormal hair and the appearance of liver abscesses which are found after slaughter.

Timpanism or meteorism is defined as a digestive alteration caused by the excessive production and accumulation of gas from fermentation (carbon dioxide and methane), causing abnormal distension of the reticulum-rumen.

Conventionally, the addition of antibiotic substances (ionophores such as monensin) has maintained the above ruminal dysfunctions in a latent state. The gradual withdrawal of such substances as growth enhancers, however, has led to the appearance of these conditions, giving rise to high mortality rates or morbidity which has a negative impact on returns. The impact on farm productivity is so important that alternatives to these antibiotic substances are required.

U.S. Pat. No. 4,443,471 refers to different chemical derivatives of the M-139603 and M-139603 ruminant growth enhancers and its use in the reduction of the quantity of methane produced by ruminal fermentation.

U.S. Pat. No. 5,196,432 refers to the use of alpha-2 adrenoceptor antagonists in the treatment of ruminants affected by lactic acidosis.

U.S. Pat. No. 5,709,894 describes a food additive for ruminants comprising glutamic acid and corn fermentation products, to increase ruminal fermentation.

Patent application U.S.2003165487 describes procedures and compositions based on the amylase enzyme of *Aspergillus oryzae* to increase ruminal fermentation efficiency and prevent a harmful increase in ruminal lactic acid concentrations, promoting the growth of beneficial ruminal microorganisms.

Patent application US2004009209 covers a procedure to keep the rumen healthy in ruminants, consisting of a mixture of low-humidity molasses and a buffer agent.

Application PCT WO9119489 describes a procedure to regulate ruminal pH levels by the administration of succinic acid and other carboxylic acid salts in ruminants fed with high-energy rations.

Application PCT WO9325616 refers to a starch product encapsulated in a matrix derived from the Maillard reaction of soluble heterologous proteins and reducing sugars to improve the efficiency of microbial fermentation in the rumen of ruminant animals.

Application PCT WO2004009104 refers to a new strain of *M. elsdenii* and its use, including the prevention and treatment of lactic acidosis in ruminants.

Application PCT WO2005000035 refers to a procedure to enhance ruminal fermentation and, in particular, reduce methanogenesis, consisting of the administration of a soluble alfalfa extract obtained from fresh alfalfa.

EP 1 323 354 describes a natural feed additive based on plant material.

It is known to feed by-products of the crop and food processing industries to livestock. For instance, citrus by-product feedstuffs may be used as components of ruminant feeding systems. They contain a variety of energy substrates for ruminal microbes (Bampidis et al. Animal Feed Science and Technology, Elsevier, vol. 128, 2006, 175-217). JP-52 028922 describes a medicament that contains inter alia bitter orange peel. The medicament is fed to horses, cows or poultry.

The inventors of this application have discovered that a mixture of citric flavonoids, specifically naringin, bitter orange extract and sepiolite is capable of regulating the microbial fermentation processes derived from the administration of concentrated rations in ruminants, increasing the efficiency of the microbial fermentation processes, and limiting the growth of certain species directly related to ruminal acidosis processes, specifically *S. bovis*.

Thus, the present invention relates to the use of a mixture comprising naringin, bitter orange extract and sepiolite in improving ruminal fermentation in ruminants.

In this application, "ruminant" includes bovine, ovine, goat and camelide species.

This mixture presents a series of advantages relative to the state of the art, making it highly valuable in the ruminant nutrition field. The advantages are that all the ingredients in the mixture are products of natural origin and easily obtainable. On the other hand, the mixture is easy to handle and can be prepared according to the industrial formulation procedures known to experts in the field. This mixture also has the additional advantage of limiting the growth of certain species related to the appearance of ruminal acidosis, especially *S. bovis*. Thus the present invention in particular relates to the use of said mixture for improving ruminal fermentation impaired by an imbalance of the natural bacterial flora in the rumen. The present invention also relates to the use of said mixture for preventing an impairment of ruminal fermentation that may be caused by an imbalance of the natural bacterial flora in the rumen. It is a particular purpose of using the mixture of the invention to limit the growth of bacteria causing ruminal acidosis, such as *Lactobacillus* spp, e.g. *Lactobacillus acidophilus* and especially *S. bovis*.

The mixture is active when added to feed in solid form at concentrations of 100 to 300 ppm (100 to 300 g/ton of feed). This is based on the in vitro studies in which the effect of the natural mixture was analysed at doses ranging from 100 to 300 ppm.

According to one aspect, the amount of naringin, in the mixture of the invention is 10% to 25%, preferably 15% to 25% and more preferably about 20% by weight.

According to a second aspect, the amount of bitter orange extract in the mixture of the invention is 10% to 65%, preferably 20% to 60% and more preferably about 40% by weight. It is noted that bitter orange extract comprises naringin and therefore the total amount of naringin in the mixture of the invention will be higher than the amount indicated above.

According to a third aspect, the amount of naringin, bitter orange extract and sepiolite is 100% by weight of the mixture.

In a first embodiment, this invention refers to the use of a mixture comprising 10% to 25% by weight of naringin, 10% to 65% by weight of bitter orange extract and a sufficient quantity up to 100% (the balance of the mixture) by weight of sepiolite, in improving ruminal fermentation in ruminants.

In an embodiment derived from the above, the mixture comprises 15% to 25% by weight of naringin, 20% to 60% by weight of bitter orange extract and a sufficient quantity up to 100% of sepiolite and, more specifically, 20% by weight of naringin, 40% by weight of bitter orange extract and 40% by weight of sepiolite.

The proportions indicated above (% by weight) refer to the total weight of the mixture.

In another embodiment, the use of the above mixtures regulates the microbial fermentation processes derived from the administration of concentrated food rations.

In another embodiment, the use of the above mixtures limits the growth of the bacteria causing ruminal acidosis, specifically *S. bovis*. The present invention thus also relates to the use the above mixtures for preventing or treating ruminal acidosis, including both acute and subacute forms as described herein.

In another embodiment, the use of the above mixtures optimises production in the intensive fattening of ruminants, specifically calves.

In another embodiment, the use of the above mixtures comprises adding them to feed in solid form at concentrations of 10 to 2000 ppm in weight, specifically 50 to 1000 ppm, and even more specifically, 100 to 300 ppm.

Flavonoids are a class of hydrosoluble vegetable pigments of growing medicinal interest. Naringin is a flavonoid, specifically a glycosylated flavanone, obtained from the peel of some citric fruits (grapefruit, *Citrus paradisi*, and bitter orange, *Citrus aurantium*) and largely responsible for their bitter taste. It is also found in the pulp of the fruit and in the leaves, flowers and seeds of the plant.

Some studies suggest that the biosynthesis of naringin, like other flavonones, is influenced by environmental and genetic factors, determining variations in the levels of concentration of these compounds, estimated as 15 to 18 g per kg of fresh grapefruit peel as a frequent concentration value. The quantity in peel also varies, in unripe fruit being higher than in ripe fruit.

Used in perfumery and to add flavour to sweets, beverages and bakery products, naringine continues to be used for its antioxidant and antimutagenic properties and as an oil stabiliser.

The bitter orange extract can be obtained from ground citrus fruits (especially *Citrus aurantium*) by ordinary operations of the art such as extraction, filtration, concentration, precipitation, clarification and final drying. Extraction processes can be performed in binary alcanol/water systems, wherein the alcanol is selected from methanol, ethanol, propanol and the like. Methanol is used preferably. A typical bitter orange extract will comprise 31.5 to 71.5% by weight, e.g. 45 to 55% by weight, of total flavonoids (if determined by HPLC). The flavonoids in particular include naringin, neohesperidine and poncirin. Typically, the total flavonoid content will comprise (a) 17.5 to 35.1% by weight, e.g. 25 to 27% by weight, of naringin, (b) 7.7 to 16.9% by weight, e.g. 11 to 13% by weight, of neohesperidine and (c) 2.1 to 6.5% by weight, e.g. 3 to 5% by weight, of poncirin.

In turn, sepiolite is a natural hydrated magnesium silicate which owes its origin to the calcareous sedimentation of marine fossils. It is a white or slightly yellowish clay mineral. It has been used since ancient times as a powdered toothpaste.

The mixture of the present invention is applied to ruminats that suffer from or are at risk of suffering from an impairment of ruminal fermentation. These ruminants include in particular:
1) Ruminants fed with high-concentrate (cereal) diets, e.g. to improve feed efficiency and avoid the appearance of ketosis processes, especially if the ruminant is
    a) a fattening animal under intensive system;
    b) a high producing lactating female in the lactation peak when concentrate supply attains the highest proportion; or
    c) a heavily pregnant ewe or goats bearing more than one kid whose intake capability has been restricted.
2) Ruminants subject to sudden dietary changes, especially if the change is
    a) from pastures (high-roughages) to high concentrated rations; or
    b) from low digestible starch (sorghum or corn) to a high digestibility one (wheat or barley).

For illustrative purposes, the following example is provided for a better understanding of the invention.

EXAMPLE 1

Effects of the Mixture in Calves at Doses of 100 and 300 ppm

Fermentation dynamics were analysed based on the protocol proposed by Theodorou M K et al., *Animal Feed Science and Technology*, 48 (3), p. 185-197, August 1994. The inoculum used was ruminal liquid from calves from commercial intensive fattening operations. The mixture of the invention (20% by weight of naringin, 40% by weight of bitter orange extract and 40% by weight of sepiolite was incubated with the inoculum and commercial calf feed (600 mg) supplemented with cereal straw in the usual proportions (80:20 concentrate: straw). The mixture doses were incubated in triplicate in two batches (2 calves) in hermetically sealed bottles with 800 ml of an inoculum dilution.

The test lasted for 48 hours, recording the pressure inside the bottle at 2, 4, 6, 12, 24, 36 and 48 h. Gas production was established from the pressure values. After 10 hours of incubation, one of the bottles was separated and the content was sampled for the determination of VFA and DNA isolation, used for the molecular genetics tests.

DNA extraction was performed by a QIAamp® DNA Stool Mini Kit (Qiagen Ltd, Carwley, West Sussex, UK). DNA concentration and purity (total DNA) was determined by spectrophotometer (NanoDrop®), measuring absorbance at 260 and 280 nm.

Bacterial and *S. bovis* DNA was quantified by real time PCR using an ABI PRISM® 7000 Sequence Detection System, with specific primers for total bacteria (Maeda H et al., *FEMS Immunology and Medical Microbiology*, 39 (1), p. 81-86, October 2003) and *S. bovis* (Tajima K et al., *Applied and Environmental Microbiology*, 67 (6), p. 2766-2774, June 2001). As a reference for calculating the concentration of total bacteria in the medium, we used a DNA concentrate of bacterial samples obtained by differential centrifugation of the ruminal liquid (500 g, 10 min., followed by 20.000 g, 20 min.). The abundance of *S. bovis* was expressed relative to that of total bacteria, using the $\Delta\Delta Ct$ expression described by Livak K J et al., *Methods* (San Diego, Calif.), 25 (4), p. 402-408, December 2001.

The bacterial biodiversity studies were conducted by DGGE using specific primers (Nübel U et al., *Journal of Bacteriology*, 178 (19), p. 5636-5643, October 1996). Electrophoresis used an 8% acrylamide gel with a 50%-65% denaturing urea/formamide gradient, for 16 hours at 80V. The gel was stained using an Amersham Biosciences (Sweden) kit and, after scanning, the band pattern was analysed using the UPGMA (Unweighted Pair-Group Method Arithmetic averages) program.

The effect of the mixture on ruminal fermentation was analysed according to a 2×2 (mixture×dose) factorial design, considering the animal as an experimental block.

Results

1.—Gas Production

In the previously described in vitro conditions, the inclusion of the mixture in the medium had no effect on either the kinetics of VFA production or total VFA production. Neither did the experimental treatment affect the molar proportions of the most important VFAs, which showed a mean proportion of 60% acetic acid, 29% propionic acid and 9% butyric acid.

2.—Real Time Bacterial Quantitation by PCR

Table 1 shows the total DNA concentration obtained by spectrophotometry (260 nm) and we can see how the DNA concentration in the culture medium was not altered by the mixture's inclusion. The determination of the quantity of bacterial DNA by a more specific procedure, real time PCR, however, showed that the inclusion of the mixture gave rise to a significant increase in bacterial DNA, indicating an increase in bacterial growth. The existence of significant differences in microbial growth derived from the presence of the mixture, without said differences being found in gas ($CO_2+NH_3$) production or greater VFA release, indicates that the mixture has a positive effect on the microbial synthesis efficiency.

The same table also shows the concentration of copies of specific DNA sequences for *S. bovis*, having identified this bacteria as one of the main producers of lactic acid and therefore related to conditions derived from ruminal acidosis. The addition of the mixture produced a highly significant limitation of the concentration of this species in the medium, with said concentration expressed as the number of DNA copies corresponding to *S. bovis* ($2(\Delta Ct)*1000$) in relation to the total number of bacterial DNA copies or as a percentage reduction in the number of copies relative to the control medium ($2(\Delta\Delta Ct)$).

TABLE 1

Concentration of different DNA types in the culture medium calculated by real time PCR; the number of DNA 16S copies in the medium as a bacterial biodiversity index

|  |  | Control | Diet Mixture 100 | Diet Mixture 300 | RSD | Significance Diet | Significance Dose |
|---|---|---|---|---|---|---|---|
| Total DNA | (μg/ml) | 37.3 | 39.7 | 32.3 | 6.98 | ns | ns |
| Bacterial DNA | (μg/ml) | 8.19 | 24.3 | 21.5 | 2.75 | 0.0018 | ns |
| *S. bovis* | 2(ΔCt)*1000 | 4.03 | 1.17 | 1.1 | 0.84 | 0.01 | ns |
| *S. bovis* | 2(ΔΔCt) |  | 0.31 | 0.29 | 0.14 |  | ns |
| DGGE | N | 15.50 | 15.0 | 15.9 | 1.44 | ns | ns |

When we analyse the effect of the dose of the mixture on the above parameters, we find no significant differences with the concentration of the mixture. The results obtained, therefore, suggest that the initial concentrations of 100 and 300 ppm exceed the threshold of activity of said compounds on ruminal fermentation processes. On the other hand, although the study mixture altered the concentration of *S. bovis*, it did not change the biodiversity of the population. This confirms the selective effect of said substances on certain microbial populations.

3.—Conclusions and Advantages

Supplementation of the study mixture with inocula from concentrated food rations administered in commercial intensive fattening conditions gives rise to significant variations in ruminal fermentation processes.

The presence of the mixture does not alter gas or VFA production levels. However, it has a significant effect on the different microbial populations in the inoculum. While promoting significant increase in the population's synthesis levels, it significantly represses *S. bovis* growth.

The invention claimed is:

1. A method for limiting the growth of bacteria causing ruminal acidosis which comprises feeding a mixture comprising 10% to 25% by weight of naringin, 10% to 65% by weight of bitter orange extract and sufficient quantity up to 100% by weight of sepiolite, to a ruminant with ruminal acidosis so as to improve ruminal fermentation in the ruminant, wherein the bitter orange extract comprises neohesperidine and poncirin, and wherein said improvement comprises limiting the growth of bacteria causing ruminal acidosis.

2. The method of claim 1, wherein the mixture comprises 15% to 25% by weight of naringin, 20% to 60% by weight of bitter orange extract and sufficient quantity up to 100% of sepiolite.

3. The method of claim 2, wherein the mixture comprises 20% by weight of naringin, 40% by weight of bitter orange extract and 40% by weight of sepiolite.

4. The method of any one of claims 1 to 3, wherein the bitter orange extract comprises 31.5 to 71.5% of flavonoids with respect to the total weight percent of the bitter orange extract.

5. The method of any one of claims 1 to 3, wherein the bitter orange extract comprises 44 to 55% of flavonoids with respect to the total weight percent of the bitter orange extract.

6. The method of claim 4, wherein the flavonoids within the bitter orange extract comprise (a) 17.5 to 35.1% by weight of naringin, (b) 7.7 to 16.9% by weight of neohesperidine and (c) 2.1 to 6.5% by weight of poncirin and wherein the weight percentages are in reference to the total weight of the flavonoids within the bitter orange extract.

7. The method of claim 4, wherein the flavonoids within the bitter orange extract comprise (a) 25 to 27% by weight of naringin, (b) 11 to 13% by weight of neohesperidine and (c) 3 to 5% by weight of poncirin and wherein the weight percentages are in reference to the total weight of the flavonoids within the bitter orange extract.

8. The method of claim 1, wherein said improvement regulates the microbial fermentation processes in the ruminant that is administered concentrated food rations.

9. The method of claim 1, wherein the bacteria causing ruminal acidosis is *Streptococcus bovis*.

10. The method of claim 1, wherein said improvement optimises production in the intensive fattening of ruminants.

11. The method of claim 10, wherein the ruminants are calves.

12. The method of claim 1, which comprises adding the mixture to feed in solid form at concentrations of 10 to 2000 ppm in weight.

13. The method of claim 1, which comprises adding the mixture to feed in solid form at concentrations of 50 to 1000 ppm in weight.

14. The method of claim 1, which comprises adding the mixture to feed in solid form at concentrations of 100 to 300 ppm in weight.

* * * * *

UNITED STATES PATENT AND TRADEMARK OFFICE
CERTIFICATE OF CORRECTION

| | | |
|---|---|---|
| PATENT NO. | : 8,377,487 B2 | Page 1 of 1 |
| APPLICATION NO. | : 12/812208 | |
| DATED | : February 19, 2013 | |
| INVENTOR(S) | : Serra et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 249 days.

Signed and Sealed this
Seventeenth Day of September, 2013

Teresa Stanek Rea
*Deputy Director of the United States Patent and Trademark Office*